US00PP09272P

United States Patent [19]

Trees

[11] Patent Number: Plant 9,272

[45] Date of Patent: Aug. 29, 1995

[54] NEW GUINEA IMPATIENS NAMED 'BFP-347 RED'

[75] Inventor: Scott C. Trees, Arroyo Grande, Calif.

[73] Assignee: Geo. J. Ball, Inc., West Chicago, Ill.

[21] Appl. No.: 337,529

[22] Filed: Nov. 8, 1994

[51] Int. Cl.[6] ..... A01H 5/00
[52] U.S. Cl. ..... Plt./87.6
[58] Field of Search ..... Plt. 87.6

*Primary Examiner*—James R. Feyrer

*Attorney, Agent, or Firm*—Burns, Doane, Swecker & Mathis

[57] ABSTRACT

A new and distinct New Guinea impatiens cultivar named BFP-347 Red is provided. This new cultivar was the result of a controlled breeding program wherein a plant designated BFP-199 (non-patented in the United States) was pollinated by a plant designated 4039-2 (non-patented in the United States). The new cultivar forms large red flowers displaying an iridescent appearance and has medium green foliage. The new cultivar can be readily distinguished from the Anaea cultivar (U.S. Plants Pat. No. 7,840).

1 Drawing Sheet

SUMMARY OF THE INVENTION

The present invention comprises a new and distinctive Impatiens plant known as New Guinea impatiens, and hereinafter referred to by the cultivar name BFP-347 Red.

The new cultivar is the product of a planned breeding program. More specifically, the breeding program which resulted in the production of the new cultivar was carried out in a controlled environment during 1992 at Arroyo Grande, Calif., U.S.A. The female parent (i.e., the seed parent) was a plant designated BFP-199 (non-patented in the United States) which exhibits large light salmon flowers, medium green foliage, and a mounded growth habit. The male parent (i.e., the pollen parent) was a plant designated 4039-2 (non-patented in the United States) which forms large salmon flowers with a white eye on a freely flowering basis, medium green foliage, and possesses a vigorous mounded growth habit. The parentage of the new cultivar can be summarized as follows:

BFP-100×4039-2.

The seeds resulting from the above pollination were sown and plantlets were obtained which were physically and biologically different from each other. Selective study resulted in the identification of a single plant of the new cultivar. This plant had large red flowers and initially was designated BFP-347.

It was found that the new cultivar of the present invention:

(a) exhibits attractive large red flowers,
(b) forms medium green foliage,
(c) exhibits a good basal branching character, and
(d) exhibits a medium upright growth habit.

Asexual reproduction of the new cultivar by terminal or stem cuttings taken during 1993, at Arroyo Grande, Calif., U.S.A. had demonstrated that the characteristics of the new cultivar as herein described are firmly fixed and are retained through successive generations of such asexual propagation.

The BFP-347 Red cultivar has not been observed under all possible environmental conditions to date.

Accordingly, it is possible that the phenotype may vary somewhat with variations in the environment, such as temperature, light intensity, and day length.

When the new cultivar of the present invention is compared to the Anaea cultivar (U.S. Plant Pat. No. 7,840), it is found that the new cultivar exhibits larger and darker red flowers, and lighter green foliage.

When plant material of the BFP-348 Red cultivar is subjected to standard random amplified polymorphic DNA marker analysis (RAPD) using polymerase chain reaction (PCR) and a known unique set of DNA primers, it is found to exhibit a different fingerprint map when compared to that of the Anaea cultivar which confirms its genetic distinctiveness.

Plants of the new cultivar will be marketed under the Celebration trademark by Geo. J. Ball, Inc.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at West Chicago, Ill., U.S.A.

DETAILED DESCRIPTION

The chart used in the identification of colors described herein is the R.H.S. Colour Chart of The Royal Horticultural Society, London, England. The color values were determined during the third week of July, 1994. The readings were taken between 10:00 and 11:00 a.m. under 2,000 footcandles of light. The plants were produced from cuttings taken from stock plants and were grown under greenhouse conditions comparable to those used in commercial practice while utilizing a soilless growth medium and maintaining temperatures of approximately 72° F. during the day and approximately 65° F. during the night.

Propagation:

*Type cutting.*—Terminal tip.

*Time to initiate roots.*—Approximately 14 to 21 days with the shorter times generally being experienced in the summer and the longer times in the winter.

*Rooting habit.*—Fibrous and branching.

Plant description:

*Form.*—Basal branching.

*Habit of growth.*—Medium upright mounded. A mature plant commonly measures approximately 14 to 16 cm. in height and approximately 27 to 30 cm. in width.

*Foliage.*—The configuration is narrow and lanceolate. The leaves of the new cultivar commonly measure approximately 9.0 cm. in length and approximately 3.0 cm. in width. Foliage is Green Group 139A (adaxial), and Yellow-Green Group 147B (abaxial) for both BFP-347 Red and Anaea cultivars. The stem color is Yellow-Green Group 145C (abaxial); Red Group 45B (adaxial). This compares to Red Group 45B for the Anaea cultivar.

Flower description:

*Flowering habit.*—Freely flowering.

*Natural flowering season.*—Throughout the year in a greenhouse environment.

*Flowers borne.*—Above foliage arising from leaf axils.

*Flower color.*—Red Group 45A (adaxial) and Red Group 45C (abaxial). This compares to Red Group 45B (adaxial) and Red Group 43B (abaxial) for the Anaea cultivar.

*Quantity of flowers.*—Approximately 10 to 13 per stem which can be compared to approximately 9 to 12 per stem for the Anaea cultivar.

*Number of petals.*—Five.

*Flower size.*—Approximately 5.5 to 5.6 cm. in length and approximately 5.2 to 5.5 cm. in width which can be compared to a length of approximately 4.9 to 5.1 cm. and a width of approximately 4.2 to 4.6 cm. for the Anaea cultivar.

*Nectary length.*—Approximately 5.6 cm. which can be compared to approximately 4.3 cm. for the Anaea cultivar.

*Nectary color.*—Red Group 53A which can be compared to Red Group 59A for the Anaea cultivar.

*Reproductive organs.*—The anthers are fused together forming one organ that surrounds the pistil. Generally the anthers shed pollen prior to the stigma becoming receptive. The pollen color is Yellow-Orange Group 19D, the stigma color is Yellow-Green Group 154D, and the ovary color is Yellow-Green Group 144C for both the BFP-347 Red and Anaea cultivars.

I claim:

1. A new and distinct cultivar of New Guinea impatiens named BFP-347 Red substantially as herein shown and described, which:

(a) exhibits attractive large red flowers, (b) forms medium green foliage, (c) exhibits a good basal branching character, and (d) exhibits a medium upright growth habit.

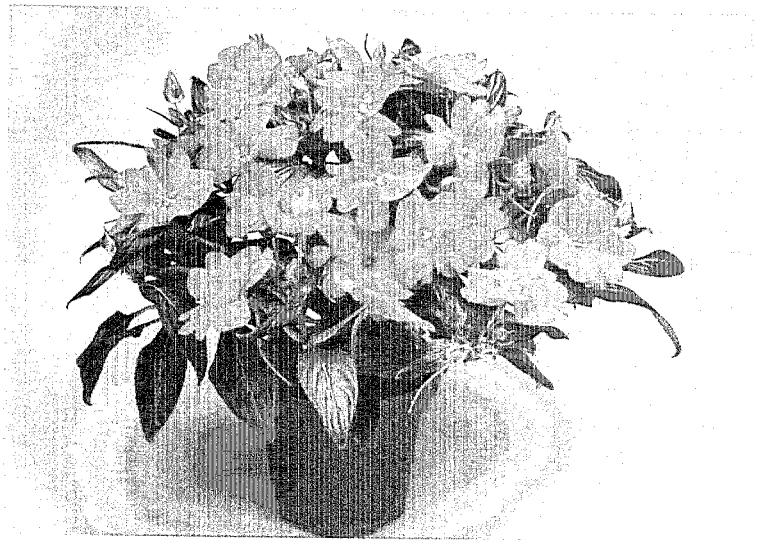

* * * * *